(12) United States Patent
Giori et al.

(10) Patent No.: US 8,084,067 B2
(45) Date of Patent: Dec. 27, 2011

(54) PHOSPHOLIPID COMPLEXES OF OLIVE FRUITS EXTRACTS HAVING IMPROVED BIOAVAILABILITY

(75) Inventors: Andrea Giori, Milan (IT); Federico Franceschi, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 12/296,696

(22) PCT Filed: Apr. 6, 2007

(86) PCT No.: PCT/EP2007/003143
§ 371 (c)(1),
(2), (4) Date: Apr. 20, 2009

(87) PCT Pub. No.: WO2007/118631
PCT Pub. Date: Oct. 25, 2007

(65) Prior Publication Data
US 2010/0068316 A1 Mar. 18, 2010

(30) Foreign Application Priority Data

Apr. 13, 2006 (EP) ..................................... 06007820

(51) Int. Cl.
*A01N 65/00* (2009.01)
*A61K 31/685* (2006.01)
*A61K 36/63* (2006.01)

(52) U.S. Cl. ........................... 424/769; 424/777; 514/78

(58) Field of Classification Search ........................ None
See application file for complete search history.

(56) References Cited

U.S. PATENT DOCUMENTS

| 2002/0004077 A1 | 1/2002 | Cuomo et al. |
| 2002/0048604 A1* | 4/2002 | Mullen |
| 2003/0017217 A1* | 1/2003 | Quintanilla Almagro et al. |
| 2005/0118232 A1* | 6/2005 | Pistolesi et al. |

FOREIGN PATENT DOCUMENTS

| DE | 3901286 A1 | 7/1990 |
| EP | 0275005 A2 | 7/1988 |
| EP | 0283713 A2 | 9/1988 |
| JP | 2002010753 A * | 1/2002 |
| WO | 0158421 A1 | 8/2001 |
| WO | 03028692 A2 | 4/2003 |
| WO | 2007013032 A2 | 2/2007 |
| WO | 2007020314 A2 | 2/2007 |

OTHER PUBLICATIONS

Meirinhos et al., "Analysis and Quantification of Flavonoidic Compounds from Portuguese Olive (*Olea europaea* L) Leaf Cultivars", Nat Prod Res 19(2):189-195 (2005).
Paiva-Martins et al., "Activity and Location of Olive Oil Phenolic Antioxidants in Liposomes", Chem and Phys of Lipids 124:23-26 (2003).
Obied et al., "Bioactivity and Analysis of Biophenols Recovered from Olive Mill Waste", J Agric Food Chem 53:823-837 (2005).
Yanyu et al., "The Preparation of Silybin-Phospholipid Complex and the Study on its Pharmacokinetics in Rats", Int'l J Pharmaceu 307:77-82 (2006).
Giacomelli et al., "Silybin and its Bioavailable Phospholipid Complex (IdB 1016) Potentiate in vitro and in vivo the Activity of Cisplatin", Life Sciences 70:1447-1459 (2002).

* cited by examiner

*Primary Examiner* — Michele Flood
(74) *Attorney, Agent, or Firm* — Porzio, Bromberg & Newman, P.C.

(57) ABSTRACT

Phospholipids complexes of olive fruits extracts or compositions containing it having improved bioavailability.

6 Claims, No Drawings

PHOSPHOLIPID COMPLEXES OF OLIVE FRUITS EXTRACTS HAVING IMPROVED BIOAVAILABILITY

CROSS REFERENCE TO RELATED APPLICATION

This is a National Stage of International Application PCT/EP2007/003143, filed Apr. 6, 2007, which claims the benefit of application Ser. No. 06007820.1, filed in Europe on Apr. 13, 2006, the disclosures of which Applications are incorporated by reference herein.

The present invention relates to phospholipids complexes of olive fruits extracts having improved bioavailability.

TECHNOLOGICAL BACKGROUND

Studies on the active principles of the *Olea europea* have been conducted for decades, and their properties were recently confirmed in experimental and clinical studies.[1]

It was reported that oleuropein, the main component detectable in the leaves, is the compound responsible for hypotension, coronary dilating and antiarrhythmic action. In one study[2] the antihypertensive, diuretic, antiaretheriosclerotic, antioxidant and hypoglicemic effect of triterpenoids isolated from *Olea europea* leaves were confirmed in a salt-sensitive genetically hypertensive rats model. Olive leaf extract also contains other synergistic phytochemicals including rutin and hesperidin. They are vital in their ability to increase the strength of the capillaries (blood vessels) and to regulate their permeability.

As far as olive oil is concerned, several studies have shown the important role of phenolic compounds contained therein. The main components, tyrosol, verbascoside and hydroxytyrosol, are potent inhibitors of LDL oxidation in vivo,[3-4] which is linked to the formation of atherosclerosis plaques that are postulated to contribute to the development of coronary heart disease. Hydroxytyrosol has been reported to reduce, alone, the risk of coronary heart diseases and atherosclerosis[5-6], being in vitro a potent and dose-dependent inhibitor of copper sulfate-induced oxidation of LDL. These results were also obtained in the animal model.[7] Verbascoside has been proved to possess potent scavenging actions on superoxide anions and hydroxyl radicals,[8-9] and also to act an antioxidant to inhibit the peroxidation of mouse liver microsome, rat liver mitochondria, the emolysis of erythrocytes induced by radicals; its antioxidant potential has been revealed in many other experimental models.

Recent studies have demonstrated that virgin olive oil phenolic components, such as hydroxytyrosol and its secoiridoid derivatives and metabolites—namely compounds with an ortho-diphenolic structure—exert strong antioxidant, as well as other biologically relevant effects.[10-11] Although most of these results have been obtained in in vitro systems,[12-13] evidence of the biological activities of olive oil phenolics in vivo is also accumulating.[14-15] Hydroxytyrosol (HT) is apparently the most active of olive phenols, it has been shown to be dose-dependently absorbed in humans, though to different degrees according to its formulation. As an example, its incorporation into a yoghurt decreases its bioavailability when compared to that after administration as a natural component of extra virgin olive oil.[16]

Therefore, it is highly desirable to find olive fruits extracts derivatives having improved bio availability.

Complex compounds of vegetable extracts or of purified components thereof with natural, synthetic or semi-synthetic phospholipids, have been disclosed, e.g., in EP 209 038, EP 275 005, EP 283 713, EP 1 035 859 and EP 1 140 115. The mentioned complexes improve the plasma bioavailability of the extract or purified component, due to their lipophilicity. EP 275 005 states that the formation of the complexes is carried out in an aprotic solvent. EP 1 140 115 generically mentions ethanol among the various solvents that can be used of the preparation of mentioned complexes, but does not provide preparation examples which make use of ethanol as the solvent. Furthermore, the complexes disclosed are phospholipid complexes of proanthocyanidin A2, which are quite different in the chemical structure with respect to the phospholipids complexes of olive fruits extracts of the present invention.

DISCLOSURE OF THE INVENTION

The present invention relates to phospholipids complexes of olive fruits extracts.

It has been found that the phospholipids complexes of the invention provide higher systemic levels of parent agent than unformulated olive fruits ethanol extracts.

Therefore, the present invention relates to phospholipids complexes of olive fruits extracts having improved bioavailability. In a first embodiment, the invention relates to phospholipids complexes of olive fruits aqueous extracts; in a second embodiment, the invention relates to phospholipids complexes of olive fruits ethanol or water-ethanol extracts.

According to the invention, phospholipids of either vegetable or synthetic origin can be used; particularly preferred are soy phospholipids, such as phosphatidyl choline, phosphatidyl serine, phosphatidyl ethanolamine.

According to the invention, the complexes are prepared by adding the phospholipid to olive fruits extracts dissolved in a protic solvent, more particularly adding the phospholipid to the ethanol solution of the extract of olive fruits, under reflux and with stirring. The resulting suspension is concentrated under reduced pressure to a residue which is then dried. The ratio of phospholipids to olive fruits extracts is in the range from 10 to 1 w/w, a more preferable mole ratio being 5:1 w/w.

The present invention also relates to pharmaceutical compositions containing as the active principle one of the phospholipids complexes of olive fruits extracts according to the invention, in admixture with a suitable pharmaceutical carrier.

The present invention further relates to the use of the phospholipids complexes of olive fruits extracts of the invention for the preparation of medicaments having chemopreventive, antioxidant and cardiovascular-diseases preventive actions.

The following examples further illustrate the invention.

EXAMPLES

Preparation of Olive Fruits Extracts

The olive fruit extract used in examples 3 and 4 is prepared as follows. Fresh *Olea europaea L.* fruits (olives) are crushed, kneaded and centrifuged to remove oil and part of the vegetation water. The resulting material (olive pomace) is then extracted with aqueous ethanol (ethanol:water 6:4) at 60° C. and the exhausted pomace is discharged. The extracts are filtered, pooled and concentrated to remove ethanol and water-insoluble impurities are removed by centrifugation. The clarified solution is evaporated under reduced pressure to obtain a dry olive fruit purified extract (total phenols content by Folin-Ciocalteau assay: 9.5% w/w).

This extract is further purified on an adsorption resin to obtain a total phenols content of 30% w/w (Folin-Ciocalteau assay) and is then used in examples 1 and 2.

The preparation of the extract used in example 5 is similar to that of the extract used in examples 3 and 4, the only difference being that olive pomace is extracted with pure water.

The leaves extract used in examples 6 and 7 is instead prepared by extracting *Olea europaea L.* leaves with aqueous ethanol (ethanol:water 9:1) at 70° C. The extracts are filtered, pooled and concentrated to remove ethanol and water-insoluble impurities are removed by centrifugation and discarded. The clarified solution is dried under reduced pressure to obtain a dry olive leaf purified extract (polyphenols content by HPLC assay: 20.8% w/w), which is used in example 6. This extract can be further purified on an adsorption resin so as to obtain a total phenol content of 41.6% w/w (HPLC assay), then used for example 7.

Example 1

Preparation of Phospholipid Complex of an Olive Fruits Purified Ethanol Extract

Soy phospholipid (150 g) is slowly added to refluxing ethanol (1.6 l) under mechanical stirring. The suspension is refluxed for 1 hour with stirring, then a solution of 50 g of olive fruit purified extract (total phenols by Folin-Ciocalteau assay: 30% w/w; HPLC assay: verbascoside 7.38% w/w) in 100 ml of aqueous alcohol (ethanol-water 7.5:2.5) kept at 60° C. is added. After completion of the addition, the mixture is refluxed under stirring for 1 hour, then filtered. The resulting solution is concentrated by distillation to 70% w/w dry residue, then dried under vacuum at 40° C. for 68 hours.

158 g of product are obtained having 8.86% w/w total phenol content by Folin-Ciocalteau assay and 2.24% w/w verbascoside content by HPLC assay.

The solubility of the product in organic solvents is noticeably different from the starting extract. In fact, while the starting purified extract is insoluble in methylene chloride, chloroform and acetone and only partially soluble in ethanol, the complexed extract is soluble in methylene chloride and chloroform and insoluble in acetone and ethanol.

$^1$H, $^{13}$C and $^{31}$P-NMR spectra confirm complex formation. Most significant data from $^{31}$P-NMR analysis are reported in Table 1. Not-complexed phospholipids have a sharp signal in the $CDCl_3$ $^{31}$P-NMR spectrum at δ 0.3 as shown for entry 1 and 3 in Table 1. Complexed phospholipids, on the contrary, have a much broader signal at δ 0.7 (vide Δ values) as shown for entry 2 in the same Table. $^1$H and $^{13}$C nuclei have the same behaviour as $^{31}$P in $CDCl_3$. Proton and carbon spectra are shown in Appendix.

TABLE 1

| $^{31}$P-NMR (121.380 MHz, $CDCl_3$, 30° C.) data | | |
|---|---|---|
| Product | δ (ppm) | Δ (Hz) |
| Commercial soy phospholipid | 0.3 | 2.7 |
| Olive fruit phospholipid complex | 0.7 | 18.3 |
| Admixture of olive fruit ethanol extract and soy phospholipid | 0.3 | 2.9 |

Example 2

Preparation of the Phosphatidylcholine Complex of Olive Fruits Purified Ethanol Extract 100 g of phosphatidylcholine are dissolved in 1.6 l of ethanol. The mixture is refluxed under mechanical stirring then dropwise added to a solution obtained dissolving 50 g of olive fruit purified extract (total phenols by Folin-Ciocalteau assay: 30% w/w; HPLC assay: verbascoside 7.38% w/w) in 100 ml of aqueous alcohol (ethanol-water 7.5:2.5) kept at 60° C. After completion of the addition, the mixture is refluxed under stirring for 1 hour, then concentrated to 70% w/w dry residue and finally dried under vacuum at 40° C. for 68 hours.

150 g of product are obtained having 10% w/w total phenols content by Folin-Ciocalteau UV assay and 2.46% w/w verbascoside content by HPLC assay. NMR spectra of the product are similar to those obtained in Example 1.

Example 3

Preparation of Phospholipids Complex of Olive Fruit Ethanol Total Extract 150 g of phospholipid are slowly added to 1.6 l of refluxing ethanol under mechanical stirring. After completion of the addition, the suspension is refluxed for 1 hour, with stirring. A solution of 50 g of olive fruit purified extract (total phenols content by Folin-Ciocalteau assay: 9.5% w/w) in 100 ml of aqueous alcohol (ethanol-water 7.5:2.5) kept at 60° C. is dropwise added. After completion of the addition, the mixture is refluxed under stirring for 1 hour and then filtered. The resulting solution is concentrated to 70% w/w dry residue, then dried under vacuum at 40° C. for 68 hours.

167 g of soy phospholipid complex of olive fruits total extract are obtained having 2.7% w/w total phenols content by Folin-Ciocalteau UV assay. NMR spectra of the product are similar to those obtained in Example 1.

Example 4

Preparation of Phosphatidylcholine Complex of Olive Fruits Ethanol Total Extract 100 g of phosphatidylcholine are dissolved in 700 ml of ethanol, and the mixture is refluxed under mechanical stirring. A solution of 50 g of olive fruit purified extract (total phenols content by Folin-Ciocalteau assay: 9.5% w/w) in 100 ml of aqueous alcohol (ethanol-water 7.5:2.5) kept at 60° C. is dropwise added. After completion of the addition, the mixture is refluxed under stirring for 1 hour, then the solution is concentrated by distillation under atmosphere pressure to 70% w/w dry residue, then dried under vacuum at 40° C. for 68 hours.

175 of product are obtained having 4.1% w/w total phenols content by Folin-Ciocalteau UV assay. NMR spectra of the product are similar to those obtained in Example 1.

Example 5

Preparation of Phospholipid Complex of Olive Fruit Aqueous Total Extract 100 g of phospholipid are dissolved in ethanol (1250 ml) and refluxed with mechanical stirring. 50 g of olive fruits aqueous total extract (total phenols content by Folin-Ciocalteau assay: 6.8% w/w) are slowly added to the mixture. After completion of the addition, the mixture is refluxed under stirring for 1 hour and then filtered. The resulting solution is concentrated to 70% w/w dry residue, then dried under vacuum at 40° C. for 68 hours.

139 g of product are obtained having 2.3% w/w total phenols content by Folin-Ciocalteau UV assay. NMR spectra of the product are similar to those obtained in Example 1.

Example 6

Preparation of Phosphatidylcholine Complex of Olive Leaves Ethanol Total Extract 100 g of olive leave total hydro-alcoholic extract (polyphenols content by HPLC assay: 20.8% w/w) are dissolved in a solution of 128 g of phosphatidylcholine in 2570 ml of ethanol. The resulting solution is refluxed for 1 hour, then concentrated under reduced pressure to a suspension having a 70% w/v dry residue. The product is finally dried at 40° C. under vacuum for 24 hours to yield 218 g of a light brown product (polyphenols by HPLC assay: 9.3% w/w). NMR spectra of the product are similar to those obtained in Example 1.

Example 7

Preparation of Phosphatidylcholine Complex of Olive Leaves Purified Ethanol Extract 100 g of olive leave purified hydro-alcoholic extract (polyphenols by HPLC assay: 41.6% w/w) are dissolved in a solution of 115 g of phosphatidylcholine in 2570 ml of ethanol. The resulting solution is refluxed for 1 hour, then concentrated under reduced pressure to a suspension having 70% w/v dry residue. The product is finally dried at 40° C. under vacuum for 24 hours to yield 196 g of a light brown product (polyphenols by HPLC assay: 18.8% w/w). NMR spectra of the product are similar to those obtained in Example 1.

Experimental Section

Tests were carried out to compare the bioavailability of the phospholipid complexes of the invention with that of the uncomplexed olive fruits ethanol extracts.

Bioavailability of phenols over time and dose ranges were assessed through evaluation of the urinary excretion over a 24 hour time, both as total HT and as its most representative metabolite, i.e. homovanillyl alcohol (HVAlc), after administration of a highly standardized olive fruit extract both in the uncomplexed and complexed forms with phospholipids to volunteers.

In addition, the effects of treatments on the excretion of urinary isoprostanes, an accepted marker of systemic lipid peroxidation formed by the non enzymatic oxidation of the highly unsaturated fatty acid, arachidonic acid, were evaluated.

Six healthy male volunteers that we assigned to two groups of three each one. The first group was administered with the complexes of the invention, from now on referred to as OLEASELECT™ Phytosome®. The second group was administered with a highly standardized olive fruit extract in the uncomplexed form, from now on referred to as OLEASELECT™.

All subjects were submitted for three days to a an olive oil-free diet (washout period), then respectively given either OLEASELECT™ Phytosome®, or OLEASELECT™, one capsule the first time, two capsules the second time, and four capsules the third time, with one week between each administration. Urine of 24-hours were collected the day before and the day after the treatments. Urinary volume was measured and aliquots were stored at −80° C.

The urinary concentrations of HT and its metabolite homovanillyl alcohol (HVAlc) were evaluated before and after treatment. Samples were extracted and incubated with glucuronidase and analyzed by HPLC coupled to mass spectrometry.[8] The urinary concentrations of $F_2$-isoprostanes were determined by immunoassay.[9] Each value was normalized to the concentration of creatinine (Metra Creatinine Assay Kit, Quidel) and is expressed as pg/mg creatinine. The results were analyzed for statistical significance by two-tailed Student's t test for paired data.

The group treated with OLEASELECT™ Phytosome® showed a percentage of HT and HVAlc ranging between 5.2 and 7.9. This result demonstrated a strong increase of oral bioavailability. A dose-related reduction of isoprostanes excretion was also observed.

The group treated with OLEASELECT™ alone showed a percentage of HT and HVAlc ranging between 1 and 2.3, i.e. much lower oral bioavailability.

REFERENCES

1. L. I. Somova, et al., *J of Ethno Pharm* 84, 299-305 (2003).
2. L. I. Somova, et al., *J of South African Veterinary Ass* 70, 14-17 (2003).
3. F. Visioli, et al., *Atherosclerosis* 117, 25-32 (1995).
4. F. Visioli, C. Galli, *Life Sci.* 55, 1965-1971 (1994).
5. A. Bonanome, et al., *Arterioscler. Thrombosis* 12: 529-533 (1986).
6. P. Grignaffini, et al., *Lancet* 343, 1296-1297.
7. M. Salami, et al., *Pharmachol. Res.* 31 275-279 (1995).
8. W. Panfen, et al., *J Biochem Pharmacol* 51, 687-691 (1996).
9. O. Benavente-Garcia, et al., *J Med Food* 5 (3)-125-135 (2002).
10. Visioli F, et al., *Circulation.* 2000; 102:2169-2171.
11. Brenes M, et al., *J Agric Food Chem.* 1999; 47:3535-40.
12. Visioli F, *Atherosclerosis.* 1995; 117:25-32.
13. Fito M, *Lipids.* 2000; 35:633-8.
14. Miro-Casas E, *Clin Chem.* 2003; 49:945-952.
15. Miro-Casas E, *Anal Biochem.* 2001; 294:63-72.
16. Visioli F, *J Nutr.* 2003; 133:2612-2615.

The invention claimed is:

1. Complexes of olive fruits aqueous, ethanol or water-ethanol extract with phospholipids wherein the phospholipids to olive fruits extract ratio is in the range from 10 to 1 w/w.

2. The complexes of claim 1, wherein the phospholipids are soy phospholipids.

3. The complexes of claim 1, wherein the phospholipids to olive fruits extract ratio is in the range from 5 to 1 w/w.

4. A process for the preparation of the complexes of claim 1, comprising reacting an aqueous, ethanol or water-ethanol extract of olive fruits with the phospholipids in an alcoholic solvent and isolating complexes by concentration and drying.

5. The process of claim 4, wherein the alcoholic solvent is ethanol.

6. Pharmaceutical compositions containing as an active principle a complex as claimed in claim 1, in admixture with a suitable pharmaceutical carrier.

* * * * *